(12) United States Patent
Bandarage et al.

(10) Patent No.: US 7,919,520 B2
(45) Date of Patent: Apr. 5, 2011

(54) INHIBITORS OF TACE

(75) Inventors: Upul Bandarage, Lexington, MA (US); Jon Come, Cambridge, MA (US); Emanuele Perola, Brookline, MA (US); Govinda Rao Bhisetti, Lexington, MA (US); Jeffrey O. Saunders, Concord, MA (US); Shi Kai Tian, Anhui (CN); Tiansheng Wang, Concord, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/269,429

(22) Filed: Nov. 12, 2008

(65) Prior Publication Data
US 2009/0176782 A1 Jul. 9, 2009

Related U.S. Application Data

(62) Division of application No. 10/741,164, filed on Dec. 19, 2003, now Pat. No. 7,485,664.

(60) Provisional application No. 60/434,936, filed on Dec. 19, 2002, provisional application No. 60/443,639, filed on Jan. 29, 2003.

(51) Int. Cl.
*A61K 31/40* (2006.01)
*C07D 207/00* (2006.01)
(52) U.S. Cl. ........................ 514/424; 548/541
(58) Field of Classification Search .................. 514/408, 514/424; 548/400, 541
See application file for complete search history.

(56) References Cited

U.S. PATENT DOCUMENTS

| 6,313,123 B1 | 11/2001 | Levin et al. |
| 7,485,664 B2 | 2/2009 | Bandarage et al. |

FOREIGN PATENT DOCUMENTS

| WO | 96/04242 | 2/1996 |
| WO | 00/44709 | 8/2000 |

OTHER PUBLICATIONS

M. L. Moss, et al., Drug Discovery Today, 6, 417-426 (2001), esp. p. 417.*
F. C. Nelson, et al., Exp. Opin. Invest. Drugs, 8, 383-392 (1999), esp. p. 383.*
R. C. Newton, et al., Ann. Rheum. Dis., 60, iii25-iii32 (2001)), esp. p. iii25.*
Ohta et al. "Tumor necrosis factor-alpha (TNF-alpha) converting enzyme contributes to production of TNF-alpha in synovial tissues from patients with rheumatoid arthritis" Journal of Rheumatology, 2001, vol. 28, pp. 1756-1763.*
Levin et al., "Acetylenic TACE Inhibitors Part 1. SAR of the Acyclic Sulfonamide Hydroxamates", Bioorganic Medicinal Chemistry Letters, vol. 13, No. 16, pp. 2799-2803, 2003.
Office Action dated Feb. 15, 2007, in U.S. Appl. No. 10/741,164.
Office Action dated Mar. 8, 2006, in U.S. Appl. No. 10/741,164.
Office Action dated Aug. 17, 2005, in U.S. Appl. No. 10/741,164.
Office Action dated Oct. 17, 2006, in U.S. Appl. No. 10/741,164.
Office Action dated Apr. 13, 2007, in U.S. Appl. No. 10/741,164.
Rao et al., "Novel thiol-based TACE inhibitors: Rational design, synthesis, and SAR of thiol-containing aryl sulfonamides", Bioorganic Medicinal Chemistry Letters, vol. 17, pp. 2250-2253, (2007).
Bandarage, et al., "Novel thiol-based TACE inhibitors. Part 2: Rational design, synthesis, and SAR of thiol-containing aryl sulfones", Bioorganic Medicinal Chemistry Letters, vol. 18, pp. 44-48, (2008).

* cited by examiner

*Primary Examiner* — Joseph R Kosack
(74) *Attorney, Agent, or Firm* — Michael C. Badia

(57) ABSTRACT

The present invention relates to compounds that inhibit TACE, compositions thereof, and methods of using those compounds and compositions for treating diseases.

3 Claims, No Drawings

INHIBITORS OF TACE

CROSS REFERENCE TO RELATED APPLICATIONS

This application is a divisional of U.S. patent application Ser. No. 10/741,164, filed Dec. 19, 2003, now U.S. Pat. No. 7,485,664 which claims the benefit under 35 U.S.C. §119(e) of U.S. Provisional Application 60/434,936 filed Dec. 19, 2002 and U.S. Provisional Application 60/443,639 filed Jan. 29, 2003 and the entire contents of each of the above applications are incorporated herein by reference.

TECHNICAL FIELD OF THE INVENTION

The present invention relates to compounds that inhibit TACE, compositions thereof, and methods of using those compounds and compositions for treating diseases.

BACKGROUND OF THE INVENTION

Adamalysin ("ADAM") is a subfamily of enzymes in the zinc metalloendopeptidases. ADAMs contain a disintigrin domain in addition to a metalloproteinase-like domain. At least twenty-three distinct ADAMs have been identified thus far.

ADAM-17, also known as tumor necrosis factor-alpha converting enzyme (hereinafter "TACE"), is the most well known ADAM. TACE is responsible for cleavage of cell bound tumor necrosis factor-alpha ("TNF-α"). TNF-α is implicated in many infectious and autoimmune diseases. Moreover, TNF-α is the prime mediator in the inflammatory response seen in sepsis and septic shock. There are two types of TNF-α, a type II membrane protein of relative molecular mass of 26 kD, and a soluble 17 kD form generated from the cell bound protein by specific proteolytic cleavage. The soluble 17 kD form of TNF-α is released by the cell and is associated with the deleterious effects of TNF-α. This form of TNF-α is also capable of acting at sites distant from the site of synthesis. Thus, inhibitors of TACE prevent the formation of soluble TNF-α and thus prevent the deleterious effects of the soluble factor.

Although a variety of TACE inhibitors are known in the art, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase-1) has been postulated to cause joint pain in clinical trials of MMP inhibitors.

Thus, there is a need for TACE inhibitors that are selective, orally bioavailable, non-peptidic for the treatment of diseases associated with TNF-α.

SUMMARY OF THE INVENTION

The present invention relates to compounds of formula (I):

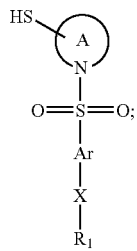

wherein:
ring A is an optionally substituted 4-7 membered heterocyclic ring containing up to 2 units of unsaturation and 0 to 3 ring heteroatoms in addition to the nitrogen atom, wherein each heteroatom is independently selected from O, S, or $NR_x$;

wherein ring A is optionally fused to aryl, cycloaliphatic, heteroaryl, or heterocyclic ring;

wherein two ring atoms in ring A are optionally bridged by 1-3 atoms to form a cycloaliphatic or heterocyclic ring, or wherein a ring atom in ring A is optionally part of another ring to form a spiro ring, wherein said spiro ring is a cycloaliphatic or heterocyclyl;

$R_x$ is H, aliphatic, OH, —C(O)—O-(cycloaliphatic or aliphatic or —C(O)-(cycloaliphatic or aliphatic);

Ar is an optionally substituted aryl or heteroaryl;

X is O, S, $NR_x$, —CH=, —C≡, or $CH_2$;

$R_1$ is C2-C8 alkynyl, optionally substituted with up to 4 substituents selected from halo, Ar, cycloaliphatic, heterocyclyl, $NH_2$, NH(cycloaliphatic or aliphatic), N(cycloaliphatic or aliphatic)$_2$, halogen, —OH, —O(cycloaliphatic or aliphatic), $NO_2$, —CN, —$CO_2H$, —$CO_2$ (cycloaliphatic or aliphatic), —O(halo-cycloaliphatic or aliphatic), or halo-(cycloaliphatic or aliphatic); and wherein up to 2 —$CH_2$— in said alkynyl, cycloaliphatic or aliphatic may be replaced with O, S, or —$NR_x$—.

The present invention also relates to compositions thereof, and methods of treating diseases using such compounds and compositions.

DETAILED DESCRIPTION OF THE INVENTION

The present invention relates to compounds having formula (I):

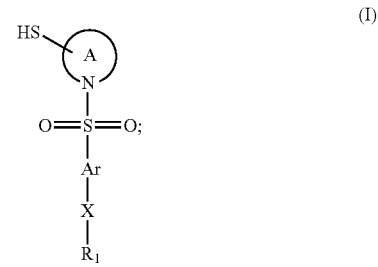

wherein:
ring A is an optionally substituted 4-7 membered heterocyclic ring containing up to 2 units of unsaturation and 0 to 3 ring heteroatoms in addition to the nitrogen atom, wherein each heteroatom is independently selected from O, S, or $NR_x$;

wherein ring A is optionally fused to aryl, cycloaliphatic, heteroaryl, or heterocyclic ring;

wherein two ring atoms in ring A are optionally bridged by 1-3 atoms to form a cycloaliphatic or heterocyclic ring, or wherein a ring atom in ring A is optionally part of another ring to form a spiro ring, wherein said spiro ring is a cycloaliphatic or heterocyclyl;

$R_x$ is H, aliphatic, OH, —C(O)—O-(cycloaliphatic or aliphatic or —C(O)-(cycloaliphatic or aliphatic);

Ar is an optionally substituted aryl or heteroaryl;

X is O, S, $NR_x$, —CH=, —C≡, or $CH_2$;

R₁ is C2-C8 alkynyl, optionally substituted with up to 4 substituents selected from halo, Ar, cycloaliphatic, heterocyclyl, $NH_2$, NH(cycloaliphatic or aliphatic), N(cycloaliphatic or aliphatic)$_2$, halogen, —OH, —O(cycloaliphatic or aliphatic), $NO_2$, —CN, —$CO_2$H, —$CO_2$ (cycloaliphatic or aliphatic), —O(halo-cycloaliphatic or aliphatic), or halo-(cycloaliphatic or aliphatic); and wherein up to 2 —$CH_2$— in said alkynyl, cycloaliphatic or aliphatic may be replaced with O, S, or —$NR_x$—.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group", as used herein, means a straight-chain or branched, substituted or unsubstituted hydrocarbon chain that is completely saturated (alkyl) or is unsaturated (alkenyl or alkynyl). Unless otherwise specified, an aliphatic group has 1 to 12 carbon atoms. Preferably, an aliphatic group has 1-6 carbon atoms. Up to two —$CH_2$— in said aliphatic may be replaced with O, S, or —$NR_x$—.

The term "cycloaliphatic" means a 3-8 membered monocyclic hydrocarbon ring or a 8-12 membered bicyclic hydrocarbon ring that is completely saturated (e.g., cycloalkyl) or that contains one or more units of unsaturation (e.g., cycloalkenyl), but which is not aromatic, and has a single point of attachment to the rest of the molecule.

The term "heteroatom" unless otherwise specified means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "unsaturated", as used herein, means a double bond or a triple bond. Each such bond constitutes one unit of unsaturation.

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". Phenyl is an example of aryl.

The term "heterocycle", "heterocyclyl", "heterocycloaliphatic", or "heterocyclic" as used herein means non-aromatic, monocyclic, bicyclic or tricyclic ring systems having in total 5 to 14 ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems, wherein at least one ring in the system is aromatic, at least one ring in the system contains one or more heteroatoms. Unless otherwise specified, such ring systems have a total of 5 to 15 ring members, wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group include halogen, —$R°$, —$OR°$, —$SR°$, 1,2-methylene-dioxy, 1,2-ethylenedioxy, phenyl (Ph) optionally substituted with $R°$, —O(Ph) optionally substituted with $R°$, —$CH_2$(Ph) optionally substituted with $R°$, —$CH_2CH_2$(Ph), optionally substituted with $R°$, —$NO_2$, —CN, —$N(R°)_2$, —$NR°C(O)R°$, —$NR°C(O)N(R°)_2$, —$NR°CO_2R°$, —$NR°NR°C(O)R°$, —$NR°NR°C(O)N(R°)_2$, —$NR°NR°CO_2R°$, —C(O)C(O)$R°$, —C(O)$CH_2$C(O)$R°$, —$CO_2R°$, —C(O)$R°$, —C(O)N$(R°)_2$, —OC(O)N$(R°)_2$, —S(O)$_2R°$, —$SO_2N(R°)_2$, —S(O)$R°$, —$NR°SO_2N(R°)_2$, —$NR°SO_2R°$, —C(=S)N$(R°)_2$, —C(=NH)—N$(R°)_2$, or —$(CH_2)_q$NHC(O)$R°$ wherein q is 0-2, and wherein each $R°$ is independently selected from hydrogen, optionally substituted C1-C6 aliphatic, an unsubstituted 5-6 membered heteroaryl or heterocyclic ring, phenyl, —O(Ph), or —$CH_2$(Ph), or wherein two occurrences of $R°$, on the same substituent or different substituents, taken together, form a 5-8-membered heterocyclyl or heteroaryl ring having 1-3 heteroatoms independently selected from nitrogen, oxygen, or sulfur. Optional substituents on the aliphatic group of $R°$ are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2$H, $CO_2$($C_{1-4}$ aliphatic), O(halo $C_{1-4}$ aliphatic), or halo $C_{1-4}$ aliphatic.

An aliphatic group or a non-aromatic heterocyclic ring may contain one or more substituents. Suitable substituents on the saturated carbon of an aliphatic group or of a non-aromatic heterocyclic ring include those listed above for the unsaturated carbon of an aryl or heteroaryl group and the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of $R^+$ are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2$H, $CO_2$($C_{1-4}$ aliphatic), O(halo $C_{1-4}$ aliphatic), or halo($C_{1-4}$ aliphatic).

Optional substituents on the nitrogen of a non-aromatic heterocyclic ring include —$R^+$, —$N(R^+)_2$, —C(O)$R^+$, —$OR^+$, —$CO_2R^+$, —C(O)C(O)$R^+$, —C(O)$CH_2$C(O)$R^+$, —$SO_2R^+$, —$SO_2N(R^+)_2$, —C(=S)N$(R^+)_2$, —C(=NH)—N$(R^+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$CH_2CH_2$(Ph), or an unsubstituted 5-6 membered heteroaryl or heterocyclic ring, or wherein two occurrences of $R^+$, on the same substituent or different substituents, taken together, form a 5-8-membered heterocyclyl or heteroaryl ring having 1-3 heteroatoms independently selected from nitrogen, oxygen, or sulfur. Optional substituents on the aliphatic group or the phenyl ring of $R^+$ are selected from $NH_2$, NH($C_{1-4}$ aliphatic)⁻, N($C_{1-4}$ aliphatic)$_2$, halogen, $C_{1-4}$ aliphatic, OH, O($C_{1-4}$ aliphatic), $NO_2$, CN, $CO_2$H, $CO_2$($C_{1-4}$ aliphatic), O(halo $C_{1-4}$ aliphatic), or halo($C_{1-4}$ aliphatic).

The term "alkylidene chain" refers to a straight or branched carbon chain that may be fully saturated or have one or more units of unsaturation and has two points of attachment to the rest of the molecule.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

According to a preferred embodiment, ring A is an optionally substituted 4, 5, or 7 membered heterocyclic ring containing up to 2 units of unsaturation and 0 to 3 ring heteroatoms in addition to the nitrogen atom, wherein each heteroatom is independently selected from O, S, or $NR_x$.

According to a preferred embodiment, ring A is an optionally substituted 4-membered heterocyclic ring containing up to 2 heteroatoms in addition to the nitrogen atom, wherein each heteroatom is independently selected from O, S, or $NR_x$.

According to a preferred embodiment, ring A is an optionally substituted 4-membered heterocyclic ring containing up to 1 heteroatoms in addition to the nitrogen atom, wherein each heteroatom is independently selected from O, S, or $NR_x$.

According to a preferred embodiment, ring A is an optionally substituted 4-membered heterocyclic ring containing up to 0 heteroatoms in addition to the nitrogen atom.

According to a preferred embodiment, ring A is a monosubstituted 4-membered heterocyclic ring containing 0 heteroatoms in addition to the nitrogen atom.

According to a preferred embodiment, ring A is an unsubstituted 4-membered heterocyclic ring containing 0 heteroatoms in addition to the nitrogen atom.

According to preferred embodiment, ring A is a 4-membered heterocyclic ring containing 0 heteroatoms in addition to the nitrogen atom and wherein two ring atoms in ring A are optionally bridged by 1-3 atoms to form a cycloalkyl or heterocyclic ring, or wherein a ring atom in ring A is optionally disubstituted to form a spiro ring, wherein said spiro ring is a cycloalkyl or heterocyclyl.

According to another preferred embodiment, ring A is an optionally substituted 5-membered heterocyclic ring containing up to 2 heteroatoms in addition to the nitrogen atom, wherein each heteroatom is independently selected from O, S, or $NR_x$.

According to another preferred embodiment, ring A is an optionally substituted 5-membered heterocyclic ring having a unit of unsaturation and containing up to 2 heteroatoms in addition to the nitrogen atom, wherein each heteroatom is independently selected from O, S, or $NR_x$.

According to another preferred embodiment, ring A is an optionally substituted 5-membered heterocyclic ring containing up to 2 heteroatoms in addition to the nitrogen atom, wherein each heteroatom is independently selected from O, S, or $NR_x$, and wherein said ring is fused to a cycloalkyl, heterocyclyl, or heteroaromatic.

According to another preferred embodiment, ring A is an optionally substituted 5-membered heterocyclic ring containing up to 1 heteroatoms in addition to the nitrogen atom, said heteroatom is O, S, or $NR_x$.

According to another preferred embodiment, ring A is an optionally substituted 5-membered heterocyclic ring containing 1 heteroatoms in addition to the nitrogen atom, wherein said heteroatom is O, S, or $NR_x$.

According to another preferred embodiment, ring A is a monosubstituted 5-membered heterocyclic ring containing 1 heteroatoms in addition to the nitrogen atom, wherein said heteroatom is O, S, or $NR_x$. Preferably, said heteroatom is O.

According to another preferred embodiment, ring A is a monosubstituted 5-membered heterocyclic ring containing 0 heteroatoms in addition to the nitrogen atom.

According to another preferred embodiment, ring A is an unsubstituted 5-membered heterocyclic ring containing 0 heteroatoms in addition to the nitrogen atom.

According to preferred embodiment, ring A is a 5-membered heterocyclic ring containing up to 3 heteroatoms in addition to the nitrogen atom and wherein two ring atoms in ring A are optionally bridged by 1-3 atoms to form a cycloalkyl or heterocyclic ring, or wherein a ring atom in ring A is optionally disubstituted to form a spiro ring, wherein said spiro ring is a cycloalkyl or heterocyclyl.

According to a preferred embodiment, ring A is an optionally substituted 6-membered heterocyclic ring containing up to 2 units of unsaturation and 0 to 3 heteroatoms in addition to the nitrogen atom, wherein each heteroatom is independently selected from O, S, or $NR_x$.

According to a preferred embodiment, ring A is an optionally substituted 6-membered heterocyclic ring containing up to 1 units of unsaturation and 0 to 3 heteroatoms in addition to the nitrogen atom, wherein each heteroatom is independently selected from O, S, or $NR_x$.

According to a preferred embodiment, ring A is an optionally substituted 6-membered heterocyclic ring containing 0 to 3 heteroatoms in addition to the nitrogen atom, wherein each heteroatom is independently selected from O, S, or $NR_x$.

According to a preferred embodiment, ring A is an optionally substituted 6-membered heterocyclic ring containing up to 2 units of unsaturation and 1 to 3 heteroatoms in addition to the nitrogen atom, wherein each heteroatom is independently selected from O, S, or $NR_x$.

According to a preferred embodiment, ring A is an optionally substituted 6-membered heterocyclic ring containing up to 1 unit of unsaturation and 1 to 3 heteroatoms in addition to the nitrogen atom, wherein each heteroatom is independently selected from O, S, or $NR_x$.

According to a preferred embodiment, ring A is an optionally substituted 6-membered heterocyclic ring containing 1 to 3 heteroatoms in addition to the nitrogen atom, wherein each heteroatom is independently selected from O, S, or $NR_x$.

According to a preferred embodiment, ring A is an optionally substituted 6-membered heterocyclic ring containing 1 to 2 heteroatoms in addition to the nitrogen atom, wherein each heteroatom is independently selected from O, S, or $NR_x$.

According to a preferred embodiment, ring A is an optionally substituted 6-membered heterocyclic ring containing 1 heteroatom in addition to the nitrogen atom, wherein each heteroatom is independently selected from O, S, or $NR_x$.

According to a preferred embodiment, ring A is an monosubstituted 6-membered heterocyclic ring containing 1 heteroatom in addition to the nitrogen atom, wherein said heteroatom is selected from O, S, or $NR_x$.

According to a preferred embodiment, ring A is an unsubstituted 6-membered heterocyclic ring containing 1 heteroatom in addition to the nitrogen atom, wherein said heteroatom is independently selected from O, S, or NR$_x$.

According to a preferred embodiment, ring A is an unsubstituted 6-membered heterocyclic ring containing 1 heteroatom in addition to the nitrogen atom, wherein said heteroatom is selected from O, S, or NR$_x$.

According to preferred embodiment, ring A is a 6-membered heterocyclic ring containing up to 3 heteroatoms in addition to the nitrogen atom and wherein two ring atoms in ring A are optionally bridged by 1-3 atoms to form a cycloalkyl or heterocyclic ring, or wherein a ring atom in ring A is optionally disubstituted to form a spiro ring, wherein said spiro ring is a cycloalkyl or heterocyclyl ring.

According to a preferred embodiment, ring A is an optionally substituted 7-membered heterocyclic ring containing 0 to 3 heteroatoms in addition to the nitrogen atom, wherein each heteroatom is independently selected from O, S, or NR$_x$.

According to a preferred embodiment, ring A is an optionally substituted 7-membered heterocyclic ring containing 2 heteroatoms in addition to the nitrogen atom, wherein each heteroatom is independently selected from O, S, or NR$_x$.

According to a preferred embodiment, ring A is an optionally substituted 7-membered heterocyclic ring containing 1 heteroatom in addition to the nitrogen atom, wherein each heteroatom is independently selected from O, S, or NR$_x$.

According to a preferred embodiment, ring A is a monosubstituted 7-membered heterocyclic ring containing 1 heteroatom in addition to the nitrogen atom, wherein each heteroatom is independently selected from O, S, or NR$_x$.

According to a preferred embodiment, ring A is a monosubstituted 7-membered heterocyclic ring containing 0 heteroatoms in addition to the nitrogen atom.

According to a preferred embodiment, ring A is an unsubstituted 7-membered heterocyclic ring containing 0 heteroatoms in addition to the nitrogen atom.

According to a preferred embodiment, ring A is a 7-membered heterocyclic ring containing 0 to 3 heteroatoms in addition to the nitrogen atom, wherein each heteroatom is independently selected from O, S, or NR$_x$, wherein two ring atoms in ring A are optionally bridged by 1-3 atoms to form a cycloalkyl or heterocyclic ring, or wherein a ring atom in ring A is optionally disubstituted to form a spiro ring, wherein said spiro ring is a cycloalkyl or heterocyclyl ring.

According to a preferred embodiment, the ring fused to ring A is selected from phenyl, triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thiophenyl, furanyl, indolizinyl, indolyl, isoindolyl, benzofuranyl, benzo[b]thiophenyl, 1H-indazolyl, benzimidazolyl, benzthiazolyl, purinyl, quinolinyl, isoquinolinyl, cinnolinyl, phthazinyl, quinazolinyl, quinoxalinyl, 1,8-naphthyridinyl, pteridinyl, carbazolyl, acridinyl, phenazinyl, phenothiazinyl, phenoxazinyl, indenyl, naphthyl, azulinyl, or anthracenyl or:

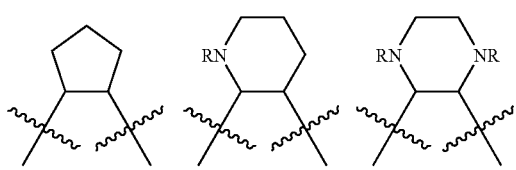

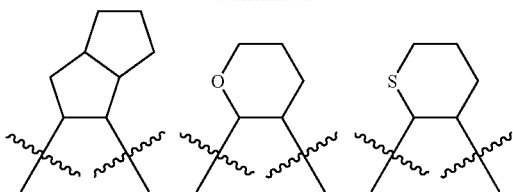

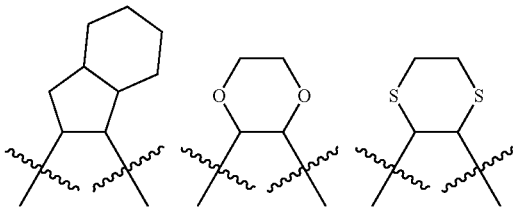

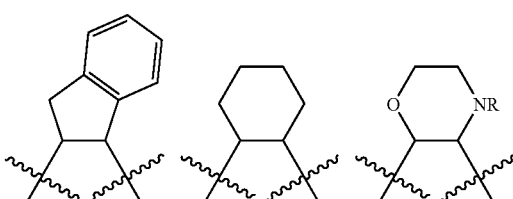

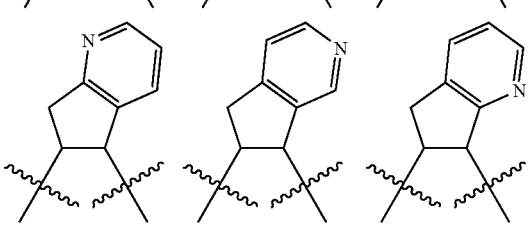

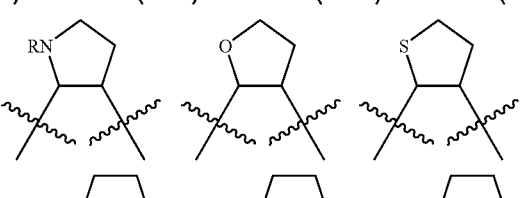

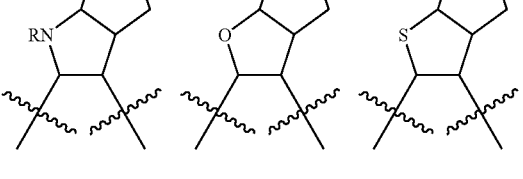

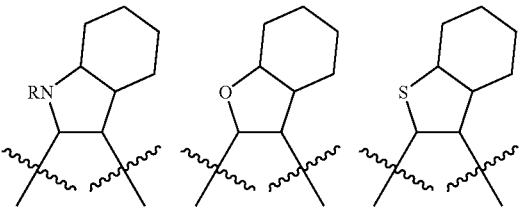

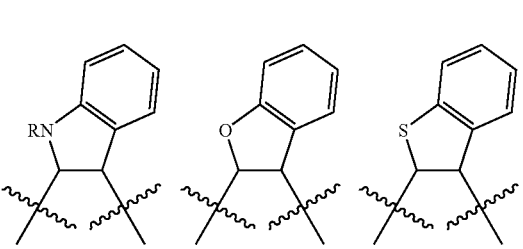

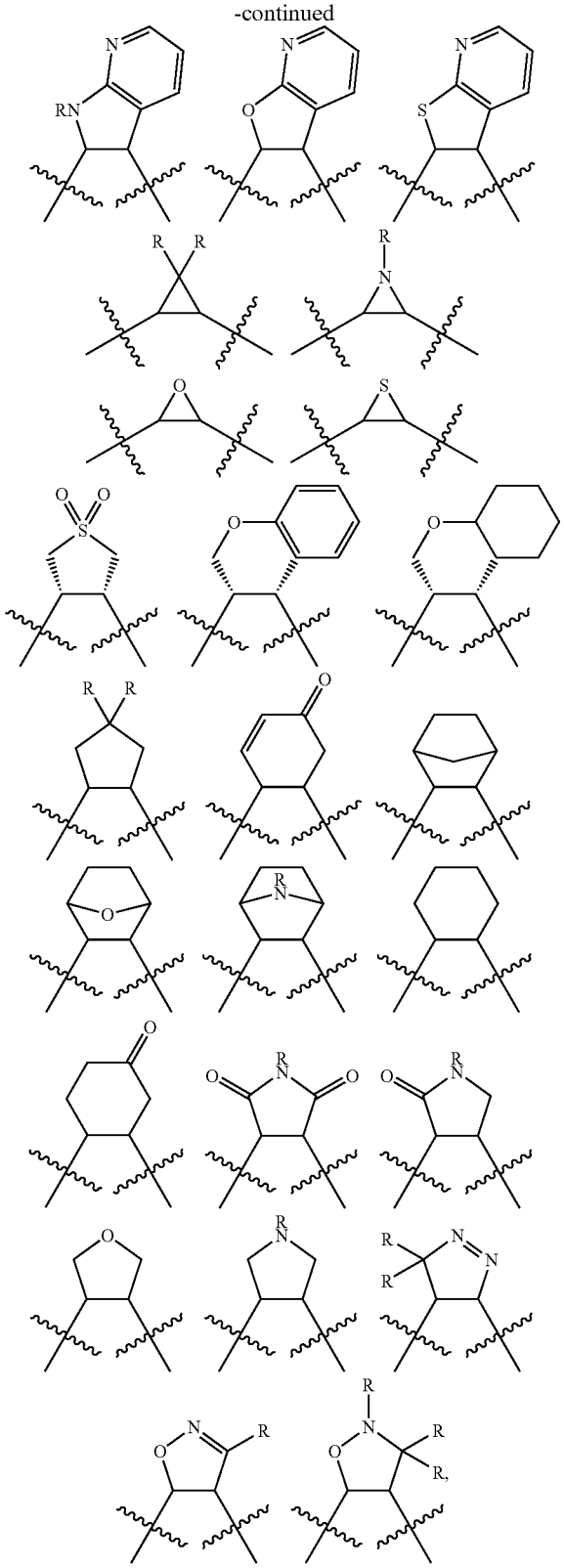

wherein R is aliphatic, aralkyl, heterocyclic, heterocyclylalkyl, heteroaryl, or heteroaralkyl.

According to another preferred embodiment, ring A, including the nitrogen atom attached to —S(O)₂— is pyrrolidinyl ring.

According to another preferred embodiment, ring A, including the nitrogen atom is:

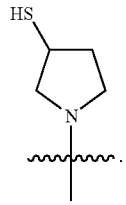

According to another preferred embodiment ring A, including the nitrogen atom is:

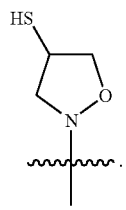

According to another preferred embodiment, ring A, including the nitrogen atom is:

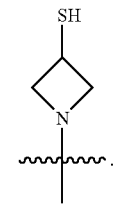

According to a preferred embodiment, ring A has up to three substituents. According to another preferred embodiment, ring A has up to two substituents. According to another preferred embodiment, ring A has up to one substituent. According to another preferred embodiment, ring A is unsubstituted.

Preferred substituents on ring A include aliphatic, cyano, halo, hydroxy, —NOH, carboxy, oxo, amido, cyanoaliphatic, hydroxyaliphatic, thioaliphatic, carboxyaliphatic, aliphatic-oxycarbonyl, aliphatic-carbonylaliphatic, aliphatic-cycloaliphatic, aliphatic-cycloaliphatic-aliphatic, aliphaticsulfonyl, aryl, aryl-aliphatic, aryl-aliphatic-oxyaliphatic, aryl(aliphatic-carbonyl)aliphatic, arylcarbamoylaliphatic, heterocyclylcarbamoylaliphatic, aliphatic-carbamoylaliphatic, cycloaliphatic-carbamoylaliphatic, diaryl-aliphatic, aryl(carboxyaliphatic)amide, arylamino, arylcarbonyl, arylsulfonyl, cycloaliphatic, cycloaliphatic-carbonyl, cycloaliphatic-alkyl, heteroaryl, heteroaryl-aliphatic, heterocyclyl, or heterocyclyl-aliphatic.

According to another preferred embodiment, ring A optionally comprises up to 3 substituents, wherein:
the first of said substituents, if present, is selected from $R^x$, $R^2$, $R^4$ or $R^5$,
the second of said substituents, if present, is selected from $R^x$ or $R^4$, and the third of said substituents, if present, is $R^X$; wherein:
  each $R^X$ is independently selected from 1,2-methylenedioxy, 1,2-ethylenedioxy, $R^6$ or $(CH_2)_n$—Y;
    wherein n is 0, 1 or 2; and
    Y is selected from halogen, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;
each $R^2$ is independently selected from $(C_1-C_6)$-straight or branched alkyl, or $(C_2-C_6)$-straight or branched alkenyl or alkynyl; and each $R^2$ optionally comprises up to 2 substituents, wherein:
  the first of said substituents, if present, is selected from $R^X$, $R^4$ and $R^{5'}$ and
  the second of said substituents, if present, is $R^X$;
each $R^4$ is independently selected from $OR^5$, $OC(O)R^6$, $OC(O)R^5$, $OC(O)OR^6$, $OC(O)OR^5$, $OC(O)N(R^6)_2$, $OP(O)(OR^6)_2$, $SR^6$, $SR^5$, $S(O)R^6$, $S(O)R^5$, $SO_2R^6$, $SO_2R^5$, $SO_2N(R^6)_2$, $SO_2NR^5R^6$. $SO_3R^6$, $C(O)R^5$, $C(O)OR^5$, $C(O)R^6$, $C(O)OR^6$, $NC(O)C(O)R^6$, $NC(O)C(O)R^5$, $NC(O)C(O)OR^6$, $NC(O)C(O)N(R^6)_2$, $C(O)N(R^6)_2$, $C(O)N(OR^6)R^6$, $C(O)N(OR^6)R^5$, $C(NOR^6)R^6$, $C(NOR^6)R^5$, $N(R^6)_2$, $NR^6C(O)R^1$, $NR^6C(O)R^6$, $NR^6C(O)R^5$, $NR^6C(O)OR^6$, $NR^6C(O)N(R^6)_2$, $NR^6C(O)NR^5R^6$, $NR^6SO_2R^6$, $NR^6SO_2R^5$, $NR^6SO_2N(R^6)_2$, $NR^6SO_2NR^5R^6$, $N(OR^6)R^6$, $N(OR^6)R^5$, $P(O)(OR^6)N(R^6)_2$, and $P(O)(OR^6)_2$;
each $R^5$ is a cycloaliphatic, aryl, heterocyclyl, or heteroaromatic; and each $R^5$ optionally comprises up to 3 substituents, each of which, if present, is $R^1$;
each $R^6$ is independently selected from H, $(C_1-C_6)$-straight or branched alkyl, or $(C_2-C_6)$ straight or branched alkenyl; and each $R^6$ optionally comprises a substituent that is $R^7$;
$R^7$ is a cycloaliphatic, aryl, heterocyclyl, or heteroaromatic; and each $R^7$ optionally comprises up to 2 substituents independently chosen from H, $(C_1-C_6)$-straight or branched alkyl, $(C_2-C_6)$ straight or branched alkenyl, 1,2-methylenedioxy, 1,2-ethylenedioxy, or $(CH_2)_n$-Z;
  wherein n is 0, 1 or 2; and
  Z is selected from halogen, CN, $NO_2$, $CF_3$, $OCF_3$, OH, $S(C_1-C_6)$-alkyl, $SO(C_1-C_6)$-alkyl, $SO_2(C_1-C_6)$-alkyl, $NH_2$, $NH(C_1-C_6)$-alkyl, $N((C_1-C_6)$-alkyl$)_2$, $N((C_1-C_6)$-alkyl$)R^8$, COOH, $C(O)O(C_1-C_6)$-alkyl or $O(C_1-C_6)$-alkyl; and
$R^8$ is an amino protecting group.

The term "amino protecting group" refers to a suitable chemical group that may be attached to a nitrogen atom. The term "protected" refers to when the designated functional group is attached to a suitable chemical group (protecting group). Examples of suitable amino protecting groups and protecting groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

According to another preferred embodiment, $R_1$ is C2-C8 alkynyl, optionally substituted with up to 3 substituents selected from halo, Ar, cycloalkyl, heterocyclyl, heteroaromatic, $NH_2$, NH(C1-C4 aliphatic), N(C1-C4 aliphatic)$_2$, halogen, OH, O(C1-C4 aliphatic) $NO_2$, CN, $CO_2H$, $CO_2$(C1-C4 aliphatic), O(halo-C1-C4 aliphatic), or halo-C1-C4 aliphatic.

According to another embodiment, $R_1$ is C2-C8 alkynyl.

According to another preferred embodiment, $R_1$ is 2-butynyl.

According to another preferred embodiment, Ar is an optionally substituted monocyclic aryl ring or a monocyclic heteroaryl ring.

According to another preferred embodiment, Ar is an aromatic ring system with substituents that enhance the ability of said ring system to engage in a π-stacking interaction. Such substituents are well known to one of skill in the art.

According to another preferred embodiment Ar is an optionally substituted phenyl or a 5-6 membered heteroaromatic ring.

According to another preferred embodiment, Ar is phenyl.

According to another preferred embodiment, Ar is triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thiophenyl, furanyl, indolizinyl, indolyl, isoindolyl, benzofuranyl, benzo[b]thiophenyl, 1H-indazolyl, benzimidazolyl, benzthiazolyl, purinyl, quinolinyl, isoquinolinyl, cinnolinyl, phthazinyl, quinazolinyl, quinoxalinyl, 1,8-naphthyridinyl, pteridinyl, carbazolyl, acridinyl, phenazinyl, phenothiazinyl, phenoxazinyl, indenyl, naphthyl, azulinyl, or anthracenyl.

According to another preferred embodiment, Ar is triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thiophenyl or furanyl.

According to another preferred embodiment Ar is triazinyl, pyrazinyl, pyrimidinyl, pyridazinyl, or pyridinyl.

According to another preferred embodiment Ar is pyridinyl.

According to another preferred embodiment,
X is O, S, or $NR_x$. According to another preferred embodiment X is —$CH_2$—. According to another preferred embodiment, X is O or S. According to another preferred embodiment, X is O. According to another preferred embodiment, X is NH. According to another preferred embodiment, X is $NR_x$.

According to another preferred embodiment, the present invention provides a compound of formula (I'):

(I')

[Structure: HS-pyrrolidine ring with Y, N-SO₂ linker to a pyridine-like ring with positions $X_1$, $X_2$, $X_3$, $X_4$, bearing X'-$R_1$]

wherein:
  Y is O or $CH_2$;
  one of $X_1$, $X_2$, $X_3$, and $X_4$ is =CH—, and each of the other three of $X_1$, $X_2$, $X_3$, and $X_4$ is independently selected from =N— or =CH—;
  X' is selected from O or $NR_x$;
  $R_x$ is H, aliphatic, OH, —C(O)—O-(cycloaliphatic or aliphatic or —C(O)-(cycloaliphatic or aliphatic);

R₁ is C2-C8 alkynyl, optionally substituted with up to 4 substituents selected from halo, aryl, heteroaryl, cycloaliphatic, heterocyclyl, NH₂, NH(cycloaliphatic or aliphatic), N(cycloaliphatic or aliphatic)₂, halogen, —OH, —O(cycloaliphatic or aliphatic), NO₂, —CN, —CO₂H, —CO₂(cycloaliphatic or aliphatic), —O(halo-cycloaliphatic or aliphatic), or halo-(cycloaliphatic or aliphatic); and wherein up to 2 —CH₂— in said alkynyl, cycloaliphatic or aliphatic may be replaced with O, S, or —NR$_x$—.

Preferred compounds of formula (I) are as follows:

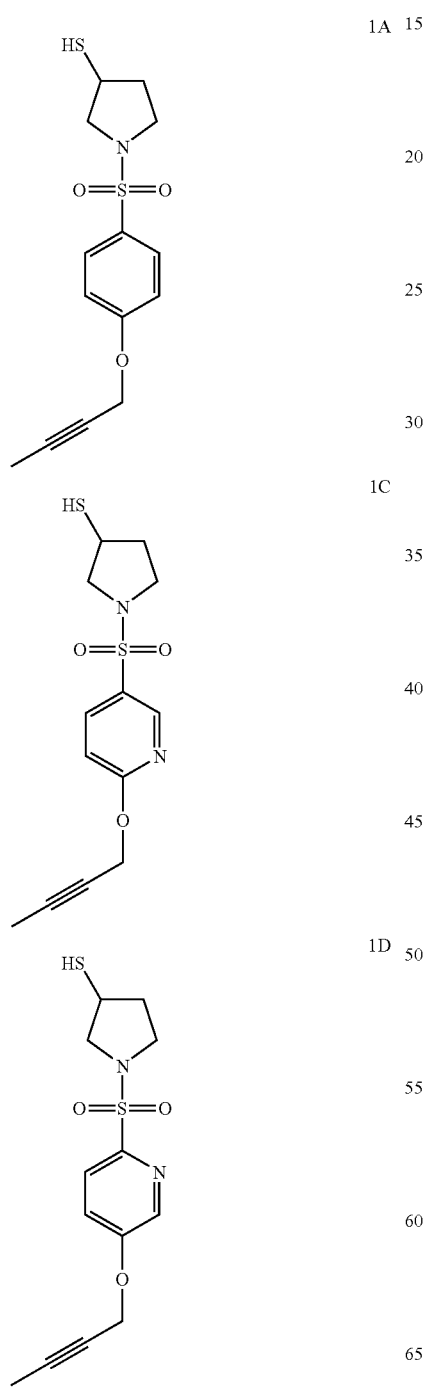

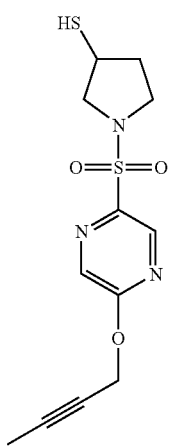

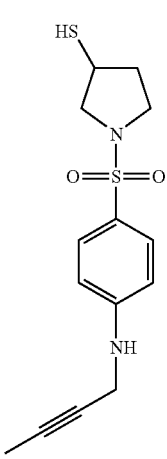

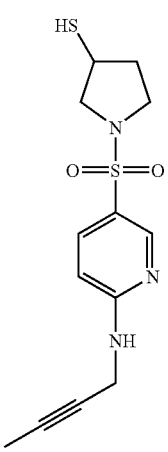

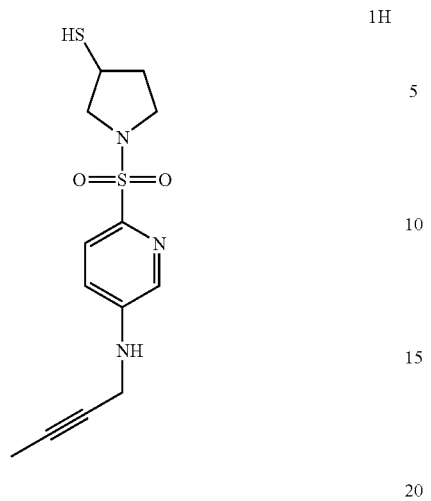
1H
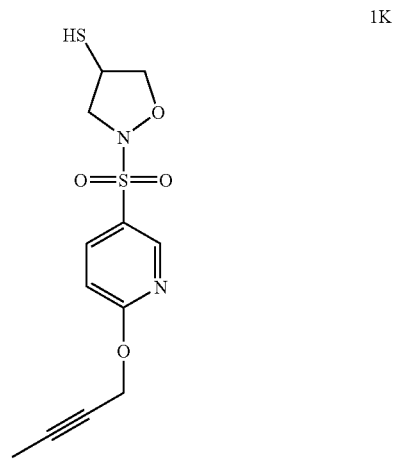
1K
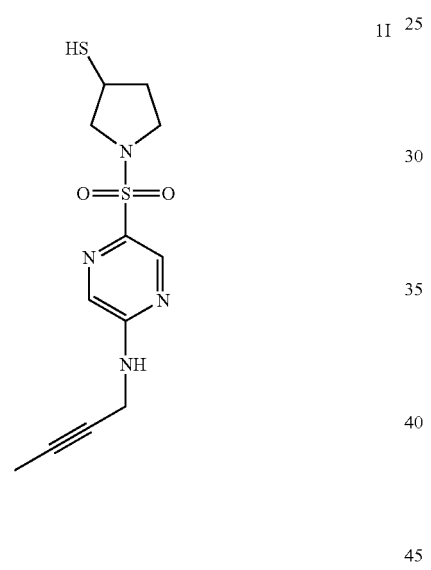
1I
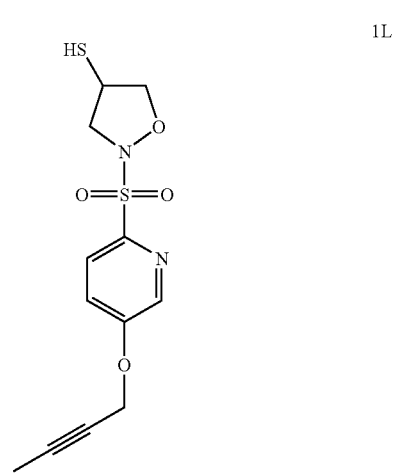
1L
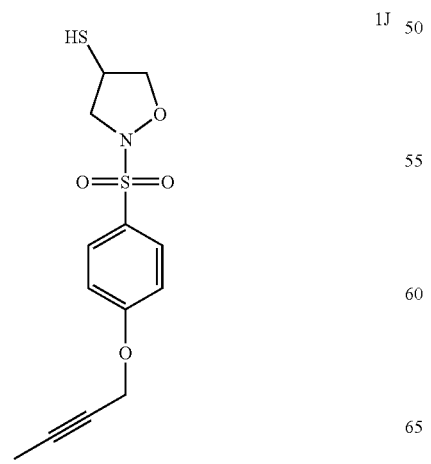
1J
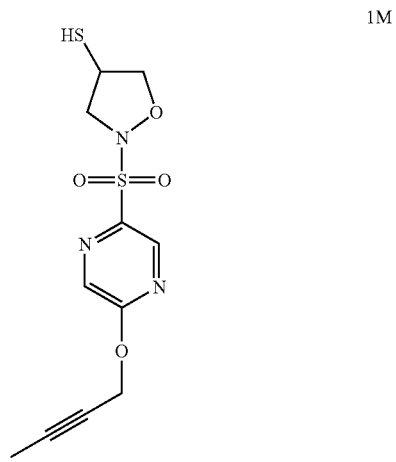
1M

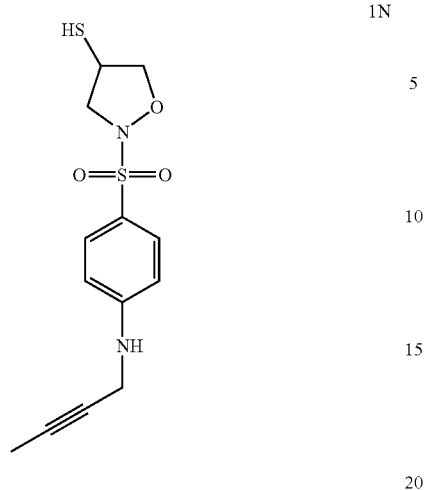
1N
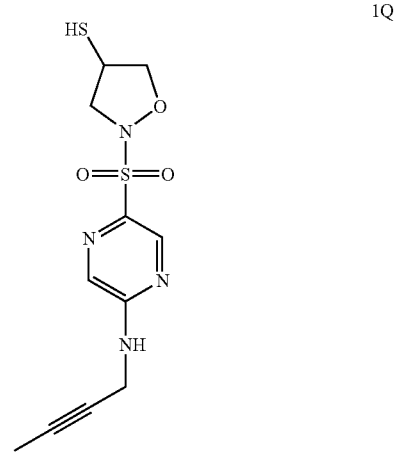
1Q
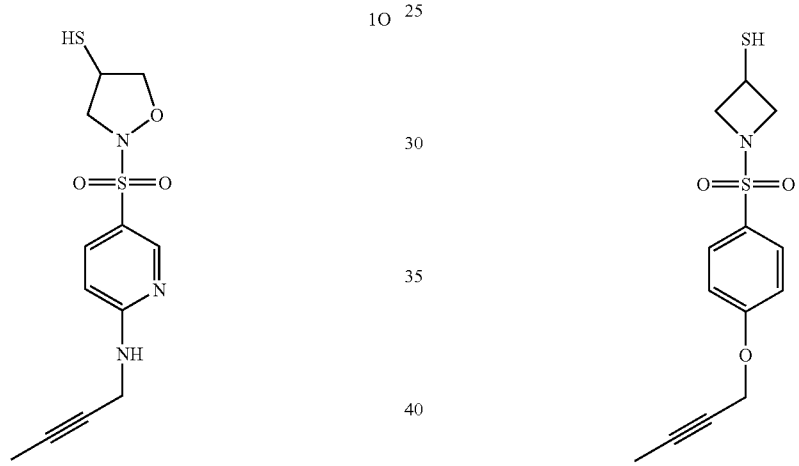
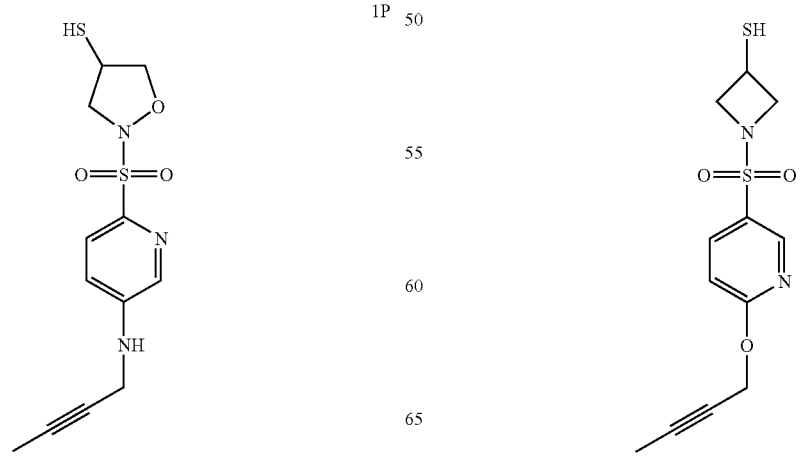

1T
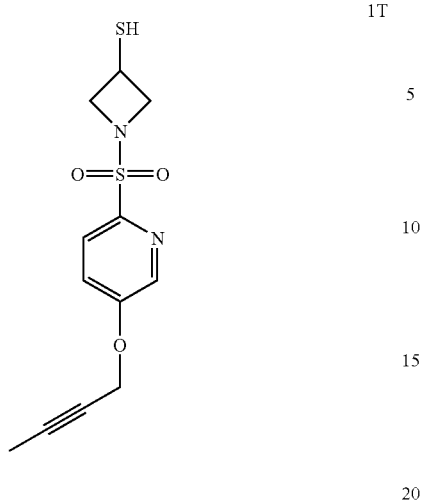
1U
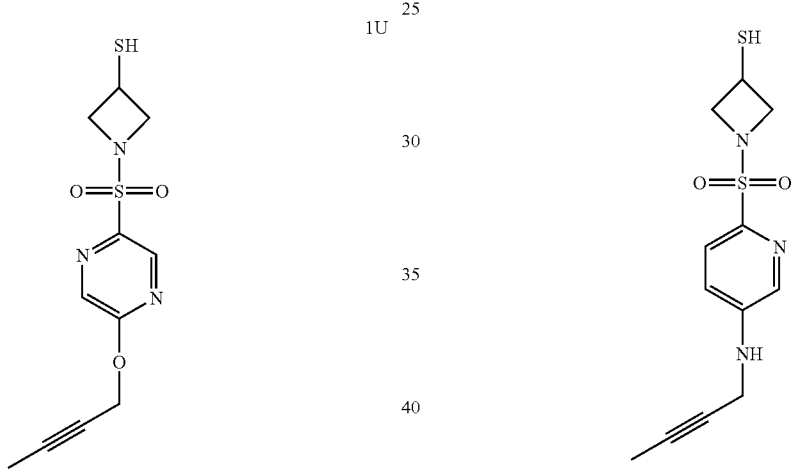
1V
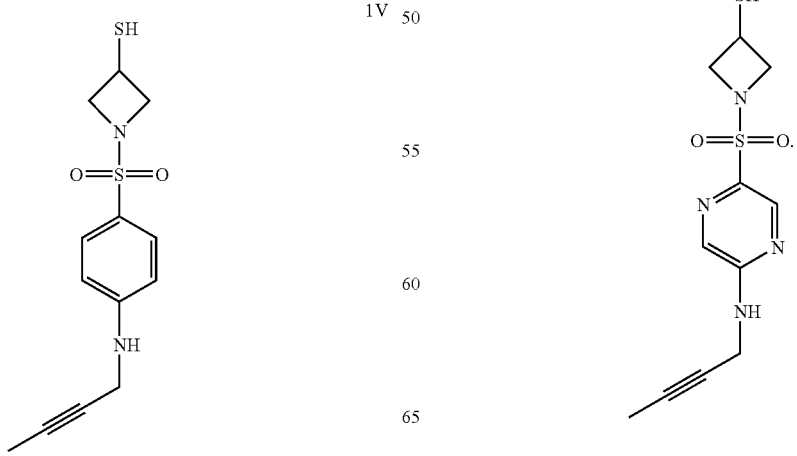
1W
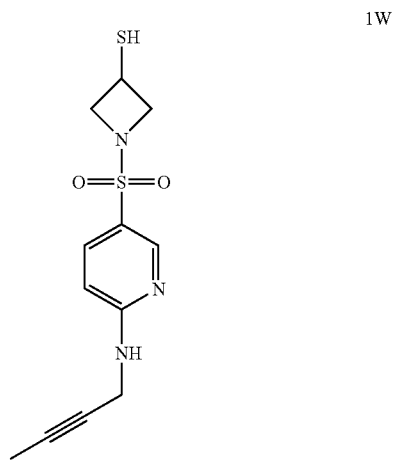
1X
1Y

According to another preferred embodiment, the present invention provides a compound of formula 1 or 1B:
1
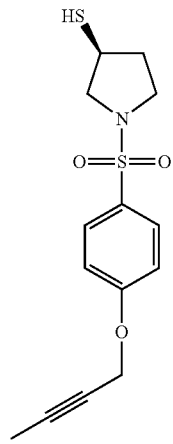
1B
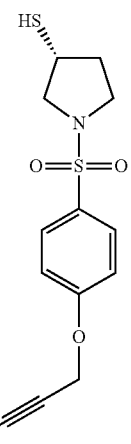
1C
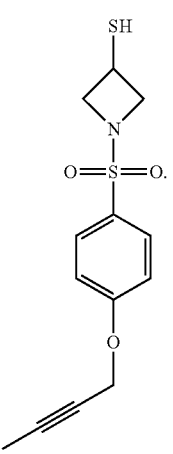
According to another preferred embodiment, the present invention provides compounds selected from Table 1 below:
TABLE 1
| Compd. No. | Structure |
| --- | --- |
| 2 | 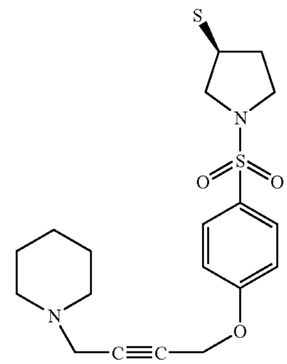 |
| 3 | 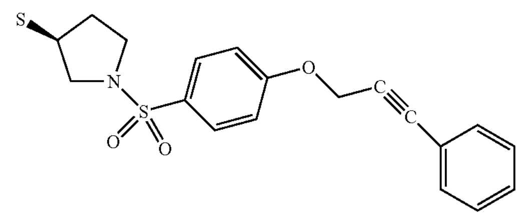 |
| 4 | 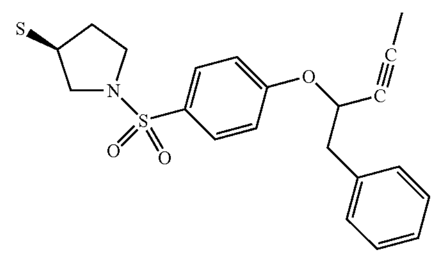 |
| 5 | 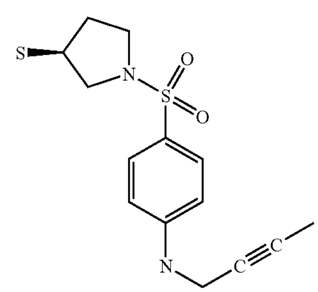 |
| 6 | 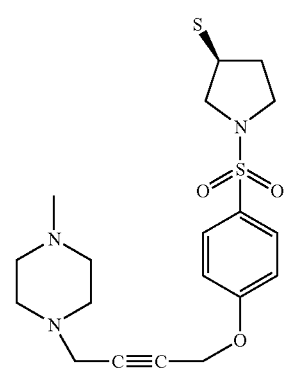 |

TABLE 1-continued

| Compd. No. | Structure |
|---|---|
| 7 | 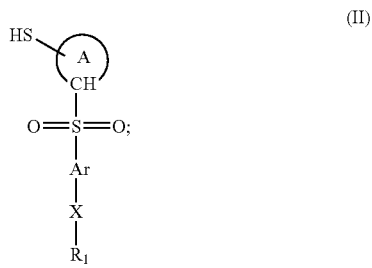 |
| 8 | 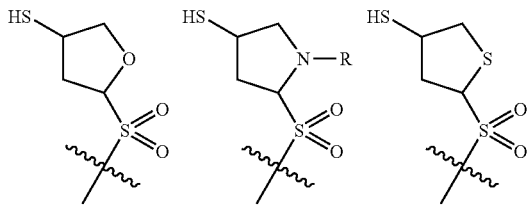 |

According to another embodiment, the present invention provides compounds of formula (II):

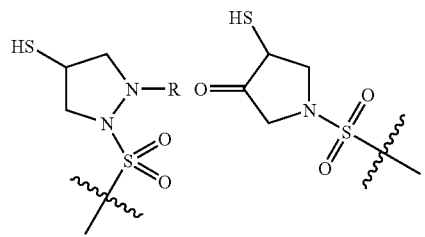
(II)

wherein:
ring A is an optionally substituted 4-7 membered cycloaliphatic ring having up to 2 units of unsaturation; or
ring A is an optionally substituted 4-7 membered heterocyclic ring having up to 2 units of unsaturation, wherein 1-3 ring atoms in ring A other than the carbon atom attached to the $S(O)_2$ group is selected from O, S, or $NR_x$;
wherein ring A is optionally fused to aryl, cycloaliphatic, heteroaryl, or heterocyclic ring;
wherein two ring atoms in ring A are optionally bridged by 1-3 atoms to form a cycloaliphatic or heterocyclic ring, or wherein a ring atom in ring A is optionally part of another ring to form a spiro ring, wherein said spiro ring is a cycloaliphatic or heterocyclyl;
$R_x$ is H, aliphatic, OH, —C(O)—O-(cycloaliphatic or aliphatic or —C(O)-(aliphatic or aliphatic);
Ar is an optionally substituted aryl or heteroaryl;
X is O, S, $NR_x$, —CH=, —C≡, or $CH_2$;
$R_1$ is C2-C8 alkynyl, optionally substituted with up to 3 substituents selected from halo, Ar, cycloaliphatic, het-erocyclyl, $NH_2$, NH(cycloaliphatic or aliphatic), N(cycloaliphatic or aliphatic)$_2$, halogen, —OH, —O(cycloaliphatic or aliphatic), $NO_2$, —CN, —$CO_2$H, —$CO_2$ (cycloaliphatic or aliphatic), —O(halo-cycloaliphatic or aliphatic), or halo-(cycloaliphatic or aliphatic); and
wherein up to 2 —$CH_2$— in said alkynyl, cycloaliphatic or aliphatic may be replaced with O, S, or —$NR_x$—.

According to a preferred embodiment, ring A in compounds of formula (II) is a 5-7 membered optionally substituted cycloaliphatic ring having up to 2 units of unsaturation.

According to a preferred embodiment, ring A in compounds of formula (II) is an optionally substituted cyclobutyl, cyclopentyl or cyclohexyl.

According to another preferred embodiment, ring A in compounds of formula (II) is cyclobutyl.

According to another preferred embodiment, ring A in compounds of formula (II) is cyclopentyl.

According to another preferred embodiment, ring A in compounds of formula (II) is cyclohexyl.

According to another preferred embodiment, ring A in compounds of formula (II) is an optionally substituted 4-7 membered heterocyclic ring having up to 2 units of unsaturation, wherein 1-3 ring atoms in ring A other than the carbon atom attached to the $S(O)_2$ group is selected from O, S, or $NR_x$.

The preferred embodiments for radicals X, Ar, and $R_1$, and substituents thereon in compounds of formula (I) are the same as those for compounds of formula (I).

According to another preferred embodiment, ring A in formula (I) and formula (II), including the thio group, nitrogen atom, and the sulfonyl group is selected from:

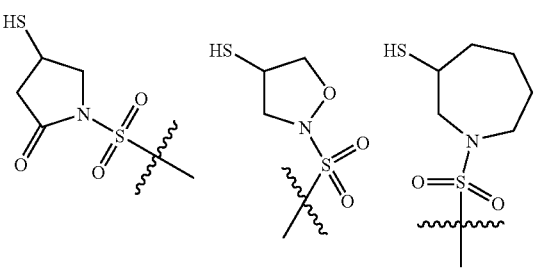

-continued

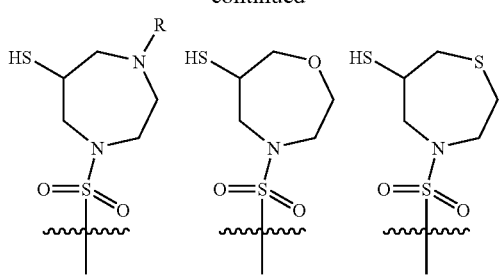

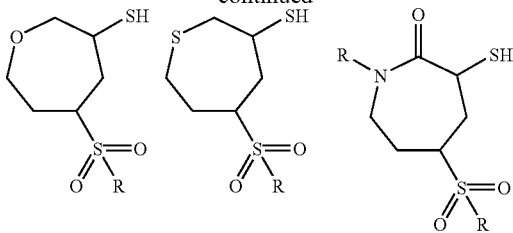

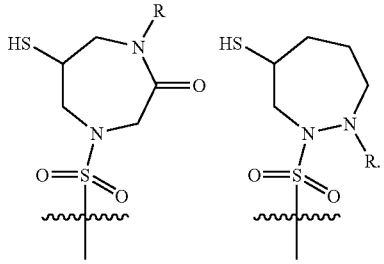

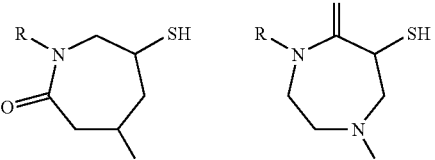

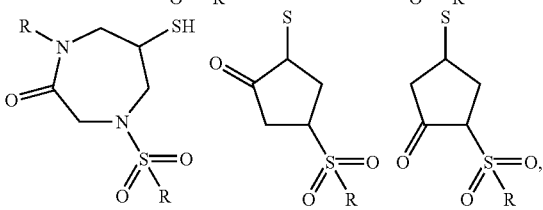

According to another preferred embodiment, ring A in formula (I) and formula (II), including the thio group, nitrogen atom, and the sulfonyl group is selected from:

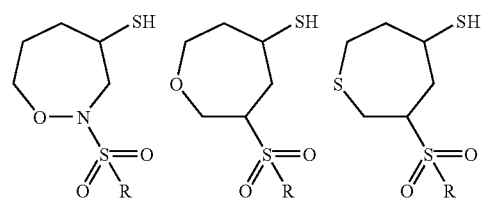

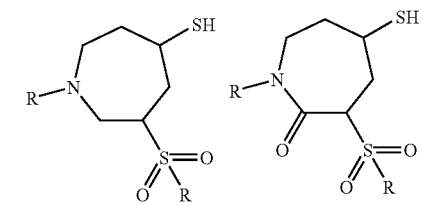

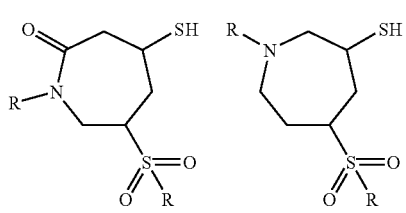

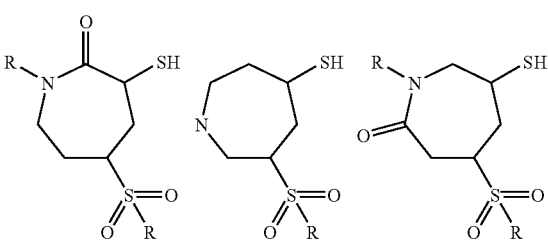

wherein R is as defined above.

According to another embodiment, the present invention provides compounds of formula (III):

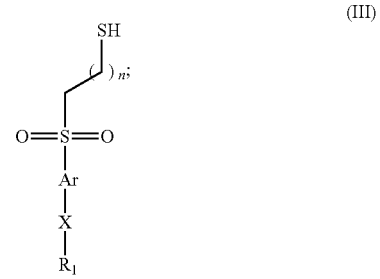

wherein:
n is 0-4;
$R_x$ is H, aliphatic, OH, —C(O)—O-(cycloaliphatic or aliphatic or —C(O)-(aliphatic or aliphatic);
Ar is an optionally substituted aryl or heteroaryl;
X is O, S, $NR_x$, —CH=, —C≡, or $CH_2$;
$R_1$ is C2-C8 alkynyl, optionally substituted with up to 3 substituents selected from halo, Ar, cycloaliphatic, heterocyclyl, $NH_2$, NH(cycloaliphatic or aliphatic), N(cycloaliphatic or aliphatic)$_2$, halogen, —OH, —O(cycloaliphatic or aliphatic), $NO_2$, —CN, —$CO_2$H, —$CO_2$(cycloaliphatic or aliphatic), —O(halo-cycloaliphatic or aliphatic), or halo-(cycloaliphatic or aliphatic); and
wherein up to 2 —$CH_2$— in said alkynyl, cycloaliphatic or aliphatic may be replaced with O, S, or —$NR_x$—.

According to a preferred embodiment, n is 1-3.
According to another preferred embodiment, n is 2.
According to another preferred embodiment, n is 1.
Preferred embodiments of Ar, X, and $R_1$ and substituents thereon in compounds of formula (III) are the same as those for compounds of formula (I).

The scope of the present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment (e.g., the brain or lymphatic system) relative to the parent species.

The compounds of the present invention may be readily prepared using methods known in the art. One such synthetic route is illustrated below in Scheme 1, wherein radical Ar is illustrated with phenyl, and ring A is illustrated with pyrrolidinyl. One of skill in the art will recognize that this synthetic route can be readily exploited for other embodiments of formula (I).

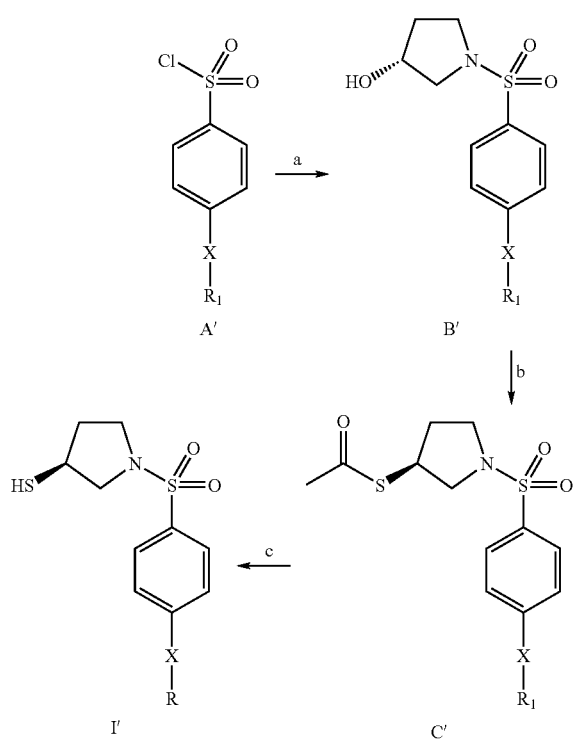

(a) (R)-pyrrolidinol, Et$_3$N, THF/H$_2$O
(b) Ph$_3$P, DEAD, CH$_3$COSH
(c) i. 10% NaOCH$_3$, MeOH ii 10% HCl.

One of skill in the art will be well aware of analogous methods for preparing compounds of formula (II) and formula (III).

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N$^+$ (C$_{1-4}$ alkyl)$_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to another embodiment, the present invention provides a method of inhibiting the in vivo cellular production/release of TNF-α in a mammal, preferably human, comprising the step administering to said mammal a composition of the present invention.

According to another embodiment, the present invention provides a method of treating a TACE mediated disease in a mammal, including human, comprising the step of treating said mammal a composition according to the present invention.

According to another embodiment, the present invention provides a method of treating a disease selected from arthritis, inflammation, inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm, congestive heart failure, myocardial infarction, stroke, cerebral ischemia, head trauma, spinal cord injury, endometriosis, general allergy, neuro-degenerative disorders, autoimmune disorders, Huntington's disease, Parkinson's disease, migraine, depression, meningitis, neuropathic pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, and septic shock in a mammal, including human, comprising the step of administering to said mammal a composition of the present invention.

According to another embodiment, the present invention provides a method of inhibiting the cleavage Of TNF-α from cell membranes in a mammal, comprising the step of administering to said mammal a compound of the present invention.

According to another embodiment, the present invention provides a method of inhibiting TACE, comprising the step of contacting said TACE with a compound of the present invention.

In order that the invention described herein may be more fully understood, the following examples are set forth. It should be understood that these examples are for illustrative purposes only and are not to be construed as limiting this invention in any manner.

EXAMPLES

Example 1

Compound 1 was synthesized according to the following synthetic scheme:

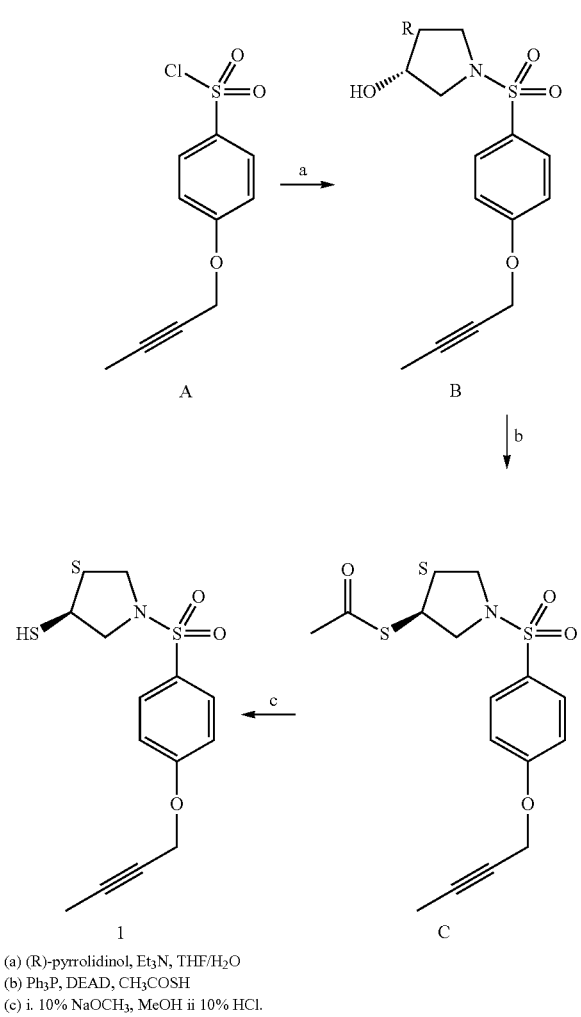

(a) (R)-pyrrolidinol, Et₃N, THF/H₂O
(b) Ph₃P, DEAD, CH₃COSH
(c) i. 10% NaOCH₃, MeOH ii 10% HCl.

I. 4-But-2-ynyloxy-N-[(R)-3-hydroxypyrrolidinyl] benzenesulfonamide (B)

4-But-2-ynyloxy-benzenesulfonyl chloride[1] A (0.3 g, 1.23 mmol) was added to a stirred solution of (R)-pyrrolidinol (0.132 g, 1.51 mmol), and triethylamine (0.4 mL) in THF (8 mL) and water (2 mL) at room temperature. The resulting mixture was stirred at room temperature for 16 h. The reaction was then diluted with ethyl acetate (50 mL) and washed with 10% HCl (10 mL) and water (25 mL). The organic layer was dried ($Na_2SO_4$), filtered and concentrated under reduced pressure to provide sulfonamide B (0.32 g, 89%) as a white solid.; ¹H NMR ($CDCl_3$, 500 MHz) δ 7.85 (d, 2H), 7.07 (d, 2H), 4.71 (q, 2H), 4.39 (m, 1H), 3.35-3.41 (m, 3H), 3.24 (m, 1H), 1.94 (m, 1H), 1.87 (t, 3H), 1.84-1.86 (m, 1H), 1.60 (m, 1H); Mass Spec. FIA MS 296 (M+1), LCMS 296 (M+1), LCMS retention time 2.5 min (10%-90% $CH_3CN/H_2O$).

4-But-2-ynyloxy-N—[(R)-3-mercaptopyrrolidinyl] benzenesulfonamide (1)

Diethyl azodicarboxylate (0.29 mL, 1.83 mmol) was added to stirred solution of B (0.27 g, 0.92 mmol), triphenylphosphine (0.48 g, 1.83 mmol) in THF (10 mL) at 0° C. The resulting yellow solution was stirred at 0° C. for 5 min and thioacetic acid (0.13 mL, 1.83 mmol) was added. The resulting solution was stirred at room temperature for 30 min. and diluted with ethyl acetate (50 mL) water (2×25 mL). The organic layer was dried ($Na_2SO_4$) and concentrated under reduced pressure to afford an oil, which was purified by flash chromatography on silica gel eluting with ethyl acetate/hexane in a gradient from (1:10) to (1:4) to provide C (0.31 g, 95.6%) as a white solid; Mass Spec. FIA MS 354 (M+1). A fresh solution of 10% sodium methoxide in methanol (2 mL) was added to a stirred solution of compound C (0.3 g, 0.85 mmol) in methanol (7 mL) and ethyl acetate (3 mL) and stirred at room temperature for 10 min. The reaction mixture was acidified with 10% HCl (25 mL) and extracted with ethyl acetate (3×25 mL). The organic layers were dried ($Na_2SO_4$), filtered and concentrated under reduced pressure. The crude product was purified by flash chromatography on silica gel eluting with ethyl acetate/hexane (1:4) to provide 1 (0.206 g, 78%) as a white solid.; ¹H NMR ($CDCl_3$, 500 MHz) δ 7.90 (d, 2H), 7.07 (d, 2H), 4.72 (q, 2H), 3.67 (dd, 1H), 3.25-3.41 (m, 3H), 3.06 (dd, 1H), 2.24 (m, 1H), 1.87 (t, 3H), 1.71 (m, 1H), 1.57 (d, 1H); Mass Spec. FIA MS 312 (M+1), LCMS 312 (M+1), LCMS retention time 3.4 min. (10%-90% $CH_3CN/H_2O$).

Example 2

The compounds of this invention were tested for TACE inhibition using the method of A. J. H. Gearing et al., (1994) Nature 370, 555; and K. M. Mohler et al., (1994) Nature 370, 218. This continuous assay uses fluorescence resonance energy transfer (FRET). TACE catalyzed cleavage of the substrate peptide liberates the fluoropore from the proximity of the adjacent quenching moiety, and an increase in fluorescence signal results.

Compound 1 was titrated in a 96 well format.

Assay: 10 mM HEPES, pH 7.5; 5 µM substrate (Bachem M-2155); 10 nM -20 nM TACE protein; 2% v/v DMSO. Fluorescence measured continuously; $K_i$ values were determined by nonlinear regression analysis. Compound 1 had a $K_i$ of 29 nM.

The invention claimed is:

1. A method of treating a TACE mediated disease in a mammal wherein said TACE mediated disease is rheumatoid arthritis comprising the step of treating said mammal with a compound having formula:

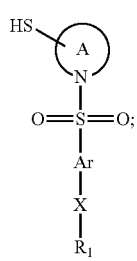

(I)

or a pharmaceutical composition thereof,
wherein:
ring A is an optionally substituted 5 membered heterocyclic ring;
$R_x$ is H, aliphatic, OH, —C(O)—O—(cycloaliphatic or aliphatic or —C(O)—(cycloaliphatic or aliphatic);
Ar is an optionally substituted aryl or heteroaryl;
X is O, S, $NR_x$, —CH=, —C≡, or $CH_2$;
$R_1$ is C2-C8 alkynyl, optionally substituted with up to 4 substituents selected from halo, Ar, cycloaliphatic, heterocyclyl, $NH_2$, NH(cycloaliphatic or aliphatic), N(cycloaliphatic or aliphatic)$_2$, halogen, —OH, —O(cycloaliphatic or aliphatic), $NO_2$, —CN, —$CO_2H$, —$CO_2$(cycloaliphatic or aliphatic), —O(halo-cycloaliphatic or aliphatic), or halo-(cycloaliphatic or aliphatic); and
wherein up to 2 —$CH_2$— in said alkynyl, cycloaliphatic or aliphatic may be replaced with O, S, or —$NR_x$—.

2. A method of treating rheumatiod arthritis, in a mammal, including human, comprising the step of administering to said mammal a compound having formula:

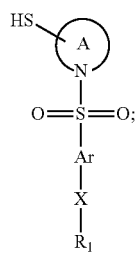

(I)

or a pharmaceutical composition thereof,
wherein:
ring A is an optionally substituted 5 membered heterocyclic ring;
$R_x$ is H, aliphatic, OH, —C(O)—O—(cycloaliphatic or aliphatic or —C(O)—(cycloaliphatic or aliphatic);
Ar is an optionally substituted aryl or heteroaryl;
X is O, S, $NR_x$, —CH=, or —C=$CH_2$;
$R_1$ is C2-C8 alkynyl, optionally substituted with up to 4 substituents selected from halo, Ar, cycloaliphatic, heterocyclyl, $NH_2$, NH(cycloaliphatic or aliphatic), N(cycloaliphatic or aliphatic)$_2$, halogen, —OH, —O(cycloaliphatic or aliphatic), $NO_2$, —CN, —$CO_2H$, —$CO_2$(cycloaliphatic or aliphatic), —O(halo-cycloaliphatic or aliphatic), or halo-(cycloaliphatic or aliphatic); and
wherein up to 2 —$CH_2$— in said alkynyl, cycloaliphatic or aliphatic may be replaced with O, S, or —$NR_x$—.

3. The method according to claim 1 or 2, comprising the step of treating said mammal with a compound or a pharmaceutical composition of said compound having formula:

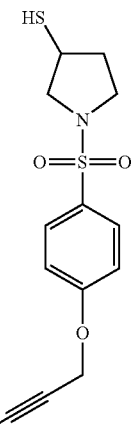

1A

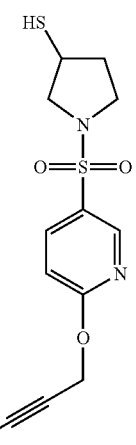

1C

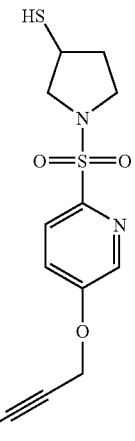

1D

1E 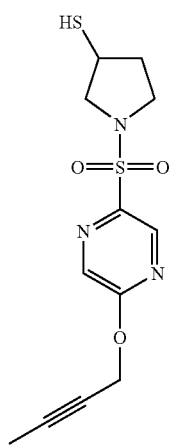
1F 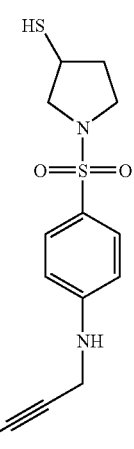
1G 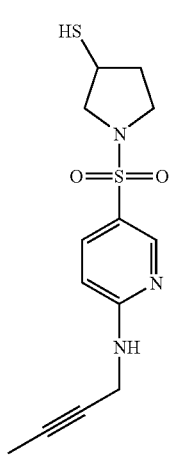
1H 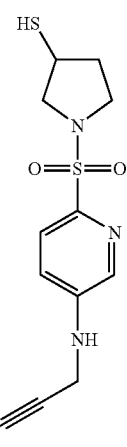
1I 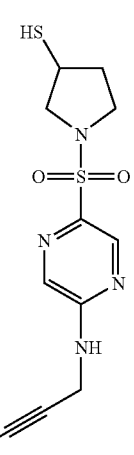
| Compd. No. | Structure |
|---|---|
| 2 | 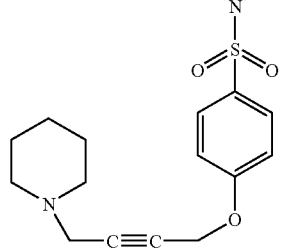 |
| 3 | 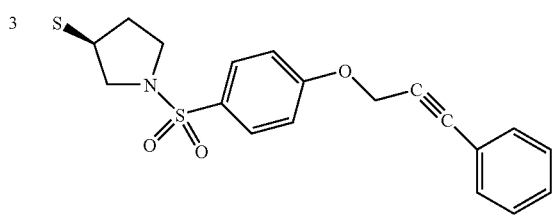 |

37
-continued
| Compd. No. | Structure |
|---|---|
| 4 | 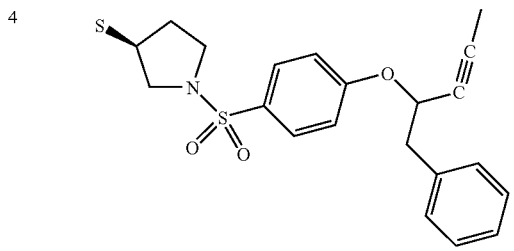 |
| 5 | 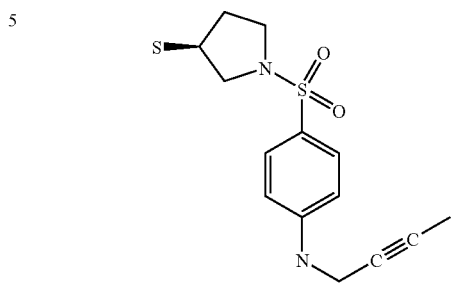 |
| 6 | 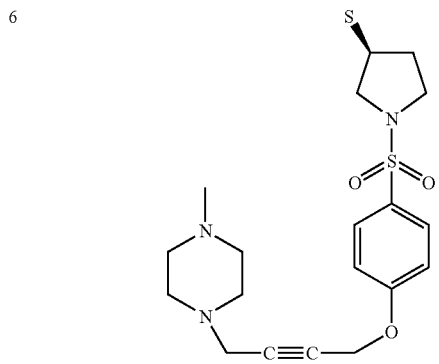 |
38
-continued
| Compd. No. | Structure |
|---|---|
| 7 | 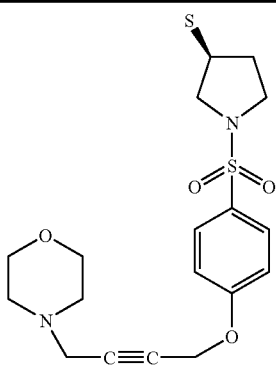 |
| 1 | 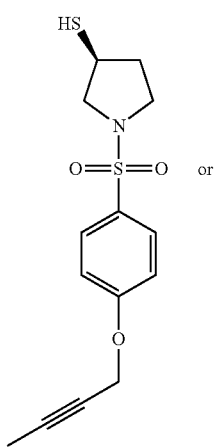 or |
| 1B | 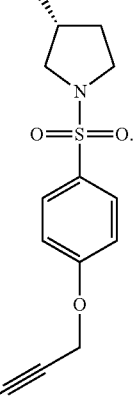 |
* * * * *